(12) United States Patent
Brown

(10) Patent No.: US 7,941,326 B2
(45) Date of Patent: May 10, 2011

(54) INTERACTIVE PATIENT COMMUNICATION DEVELOPMENT SYSTEM FOR REPORTING ON PATIENT HEALTHCARE MANAGEMENT

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 2452 days.

(21) Appl. No.: 09/810,334

(22) Filed: Mar. 14, 2001

(65) Prior Publication Data

US 2002/0133377 A1 Sep. 19, 2002

(51) Int. Cl.
G06Q 10/00 (2006.01)
(52) U.S. Cl. .................................. 705/3; 705/2
(58) Field of Classification Search .................. 705/2–4; 600/300–301
See application file for complete search history.

(56) References Cited

U.S. PATENT DOCUMENTS

| | | | |
|---|---|---|---|
| 5,517,405 A | 5/1996 | McAndrew et al. | 364/401 |
| 5,574,828 A | 11/1996 | Hayward et al. | 395/50 |
| 5,765,139 A * | 6/1998 | Bondy | 705/8 |
| 5,897,493 A * | 4/1999 | Brown | 600/300 |
| 5,918,603 A | 7/1999 | Brown | 128/897 |
| 6,139,494 A * | 10/2000 | Cairnes | 600/300 |
| 6,584,445 B2 * | 6/2003 | Papageorge | 705/3 |
| 2002/0010597 A1 * | 1/2002 | Mayer et al. | 705/2 |

* cited by examiner

Primary Examiner — Vivek D Koppikar
(74) Attorney, Agent, or Firm — Christopher P. Maiorana, PC

(57) ABSTRACT

A modular interactive system and method for customizing health education to an individual at a remote terminal to induce a modification in a health-related behavior of the individual. The automated system includes a questionnaire generator for questioning the individual to determine his or her motivational drivers and comprehension capacity. The questionnaire generator is a graphical user interface that allows a clinician to graphically attach questions to answer to action. A processor then generates a script program based on what the clinician has attached together. A profile generator receives answers entered by the individual from the remote terminal and generates a motivational driver profile and a comprehension capacity profile of the individual. A translator receives clinical data relating to a current health condition of the individual and translates the clinical data, the motivational driver profile, and the comprehension capacity profile into a profile code. An educational fulfillment bank matches the profile code to matching educational materials and transfers the matched educational materials to the remote terminal. An evaluation program evaluates educational responses of the individual and provides profile updates for targeting subsequent educational material to the individual based on the educational responses.

20 Claims, 7 Drawing Sheets ic ## INTERACTIVE PATIENT COMMUNICATION DEVELOPMENT SYSTEM FOR REPORTING ON PATIENT HEALTHCARE MANAGEMENT

FIELD OF THE INVENTION

The present invention relates generally to a modular interactive development system and method for reporting on patient management, and in particular to an automated content delivery program able to connect remote users across independent platforms to a central database of libraries whereby a patient's health can be scored dynamically.

BACKGROUND OF THE INVENTION

This invention relates to the field of health management, particularly to an automated interactive system and method for reducing the risk associated with a monitored client.

For example, the know art includes a number of health-management systems for providing outpatient services to patients with chronic health conditions such as asthma and diabetes. However, these systems are incapable of administering a treatment protocol responsive to the patient's current profile and of updating the profile in response to the administered protocol.

SUMMARY OF THE INVENTION

This invention presents a flexible and scalable system in content development for patient management healthcare. Due to the modular object oriented-structure, individual content modules ("dialogs") can be mixed into an unlimited number of updateable customized programs, addressing individual as well as co-existing disease states ("co-morbid") in any combinations, and with automated content variation for improved patient compliance. A dialog is the smallest content object in the FlexCube content structure. Its content addresses issues related to a unique set of symptoms, behaviors or knowledge related to a specific aspect of managing a certain disease referred to as an aspect of care.

In its basic format, each dialog contains questions related to signs and symptoms, behaviors and knowledge with answers categorized as high, medium or low risk answers. For each answer there is a relevant follow up, which can be a teaching statement, an acknowledgment, a motivational statement or a new question that will explore the patient's condition in more depth. While the logical branching within a dialog is driven by patient answers, no dependency exists between individual dialogs.

Dialogs are located in a common pool organized by library. From this library each individual dialog is referenced for participation (appearance) in programs and daily sessions. A dialog's behavior in a program (schedule, position, reporting) is defined at the time of the dialog creation or it is custom defined during the program content selection process. In this way dialogs maintain their integrity while being used and re-used in several client programs. They combine freely with other dialogs in user defined program selections, allowing an unlimited combination of aspects of care and co-existing diseases. Finally, they are easily accessible for revisions and updates.

The present invention provides an object-oriented dialog and modular toolkit structure that enhances quality control options. Also included are the centrally located content objects that offer overview and tracking of the currently active content, global error correction and global update of content to current standards of care. Because the present invention splits up interfaces for content creation and content selection into separate modules, the present invention exercises control over customer's access to content development in compliance with current and future Federal Drug Administration labeling. Finally the system's structure limits logical branching errors to within a dialog, thereby offering a more robust and less error prone system overall.

Since the content of a dialog and the output of a dialog is related and mapped to a specific aspect of care, the user will have the power and flexibility to model risk evaluation and outcomes reporting around custom selected aspects of care.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF PREFERRED EMBODIMENT

The present invention includes an object-oriented content structure in which the smallest content object, a care specific dialog, is located in a central library from where its characteristics (operators) are composed and referenced by a modular set of tools located at a client computer.

Figure 1:
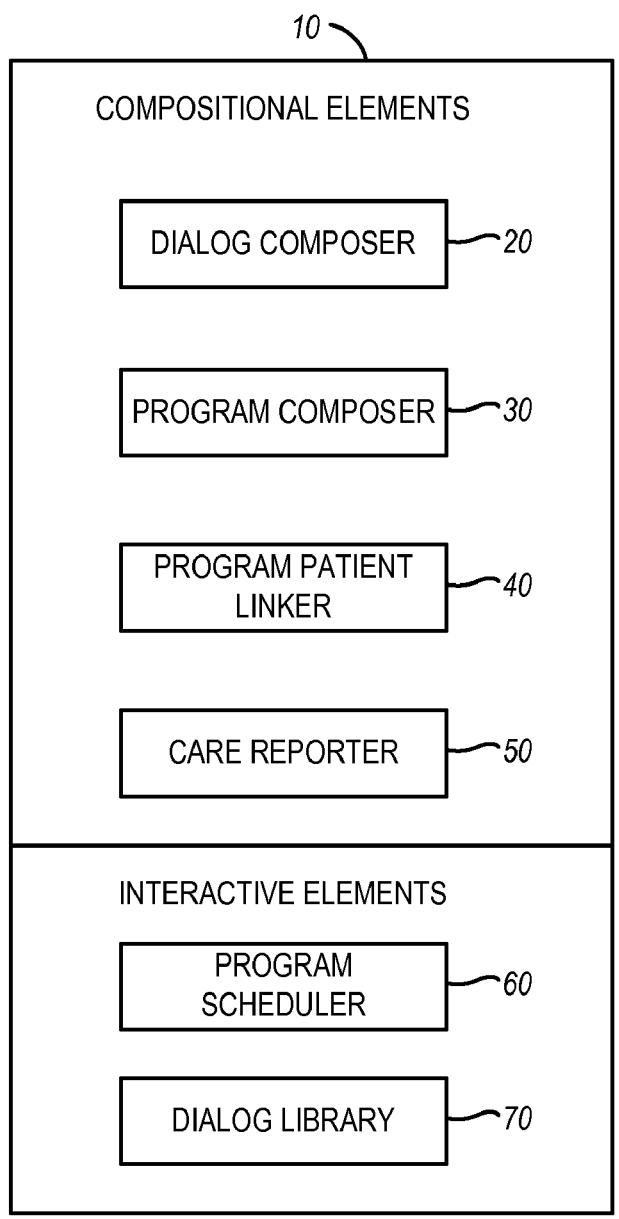
FIG. 1 is a block diagram depicting a system's compositional and referenced components.
Figure 7:
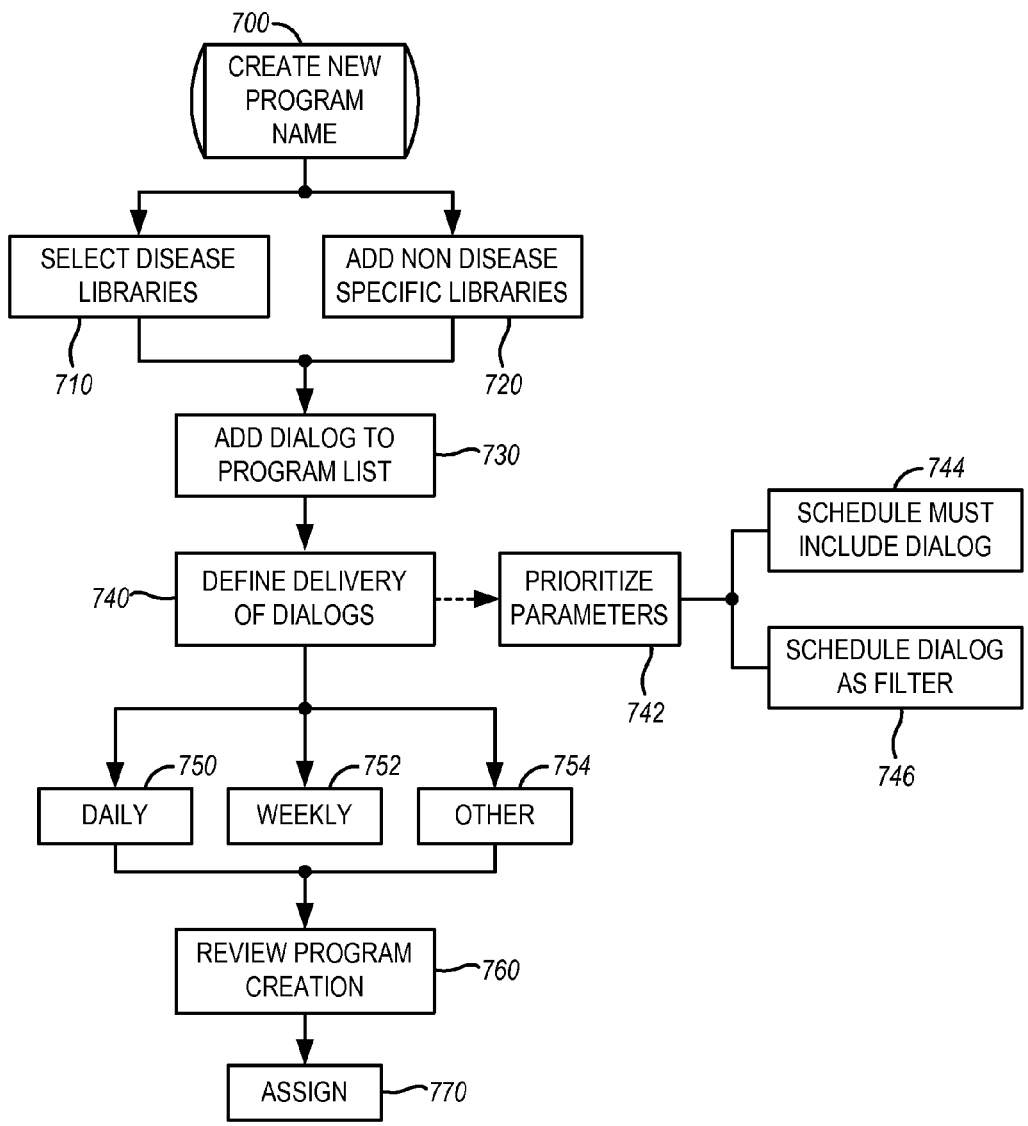
FIG. 7 is a flowchart depicting the creation of programs using a Program Composer User Interface.
Figure 9:
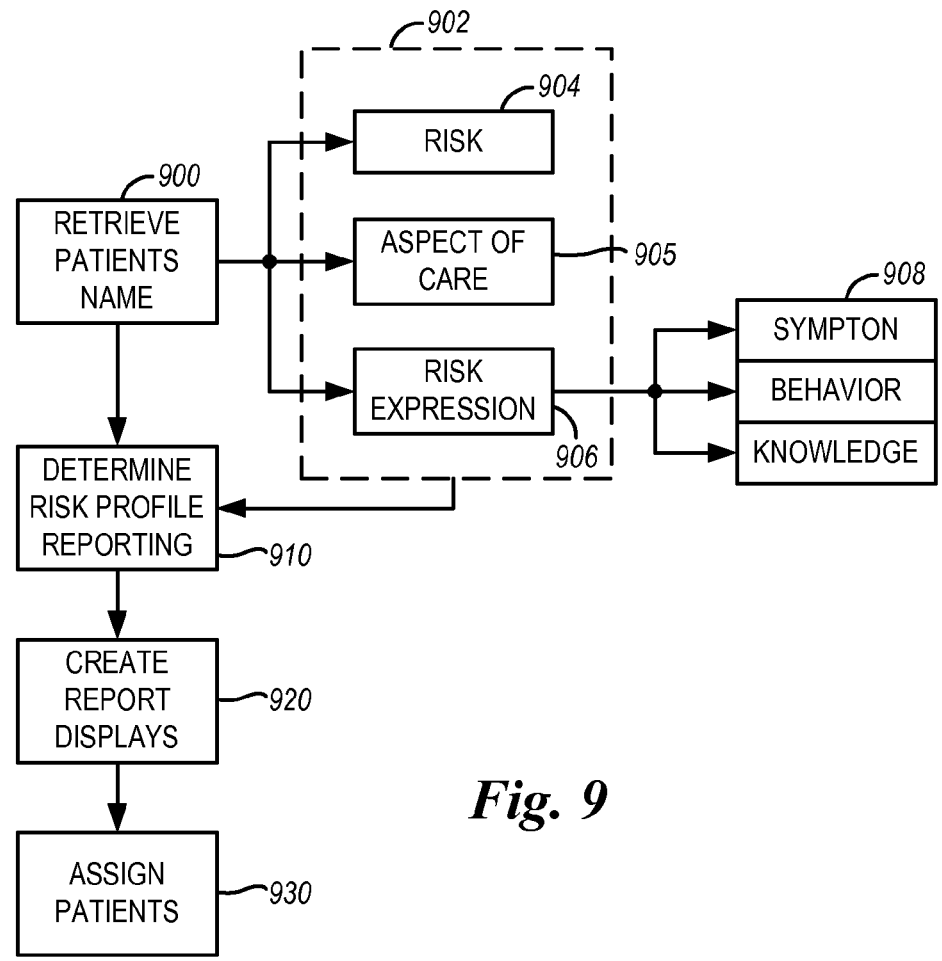
FIG. 9 is a flow chart depicting a Reporter User Interface.

FIG. 1 is a block diagram depicting a system 10's compositional and referenced components. Compositionally, the system 10 relies on four system components for dialog or program creation. Additionally, FIG. 1 illustrates two other system components that interact with the referenced components of the system. A dialog Composer 20, further referenced in FIG. 2, which is used to author dialog content by an aspect of care. A Program Composer 30, further referenced in FIG. 7, is a user interfaced click and drag assembly platform for composing programs (a virtual content defined collection of dialogs). On a computer desktop, content dialogs are selected (referenced) for use in disease/client specific programs, with program specific tagging of individual dialog attributes related to frequency (scheduling) and reporting. A Program Patient Linker 40 is a user interface integrated into the desktop on which patients are assigned to programs. During the assignment process patient identification and patient specific metrics are added to the program. A Care Reporter 50, further referenced in FIG. 9, is a user interface for easy patient result lookup, triage and trend reports. Reporting requirements set in the Program Composer 30 determine which reports are displayed.

Figure 8:
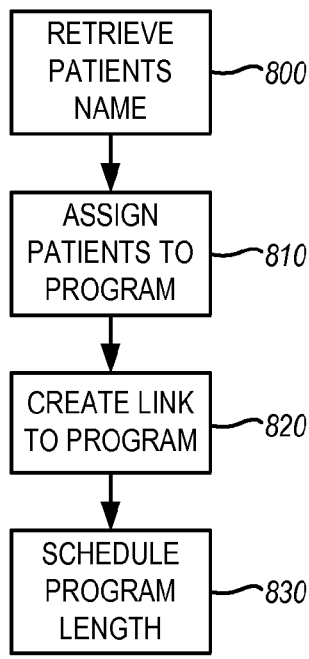
FIG. 8 is a flow chart depicting a Linker User Interface.

Compositional elements of the system 10 reference either one or both of the two remaining components of the system depicted in FIG. 1. A Program Scheduler 60, further referenced in FIG. 8, is an engine for automated scheduling of dialogs based on attributes set in the Program Composer 30, and A Dialog Library 70. The Dialog Library is the principal central location of dialog content units. Dialogs are organized into body system labeled sub-libraries and stored within the Dialog Library 70.

Figure 2:
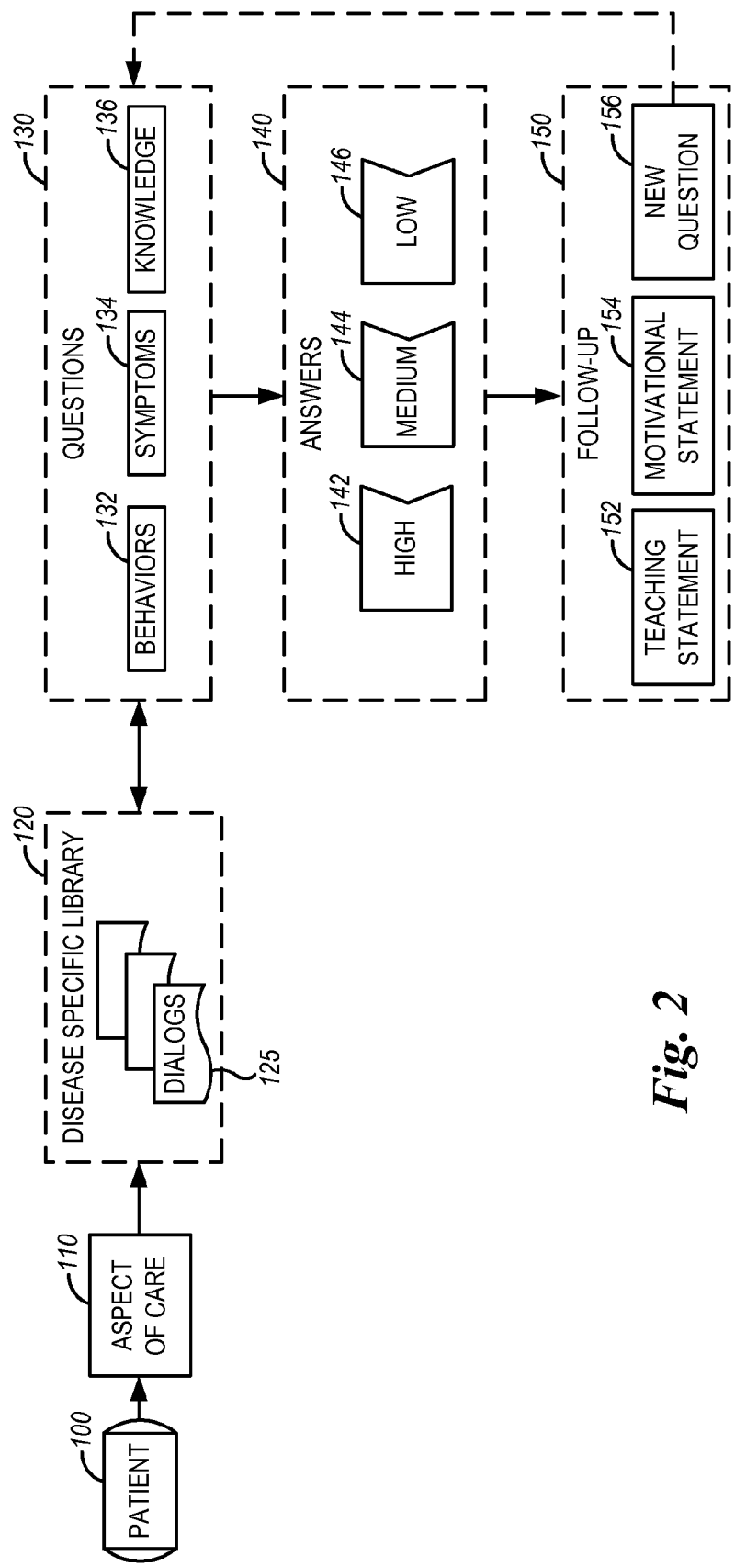
FIG. 2 is a flow chart diagram depicting the overview of dialog creation.

The structure of the system is developed from the integration of the four compositional components as referenced above with the two referenced components and begins with the creation of dialogs in the Dialog Composer 20 as depicted FIG. 2.

Figure 4:
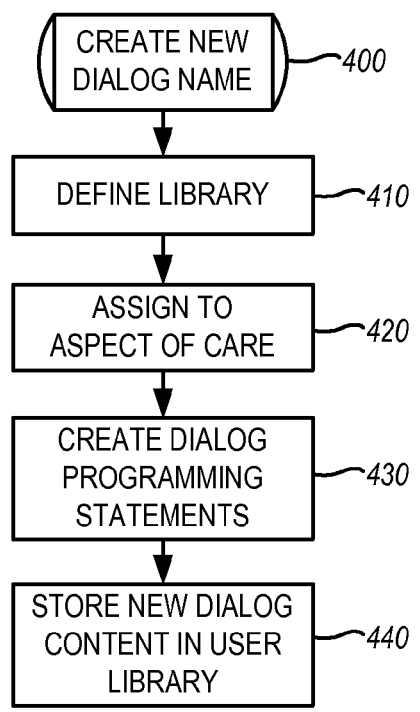
FIG. 4 is flow chart depicting the steps in creating and storing of content data from a dialog.

FIG. 2 is a flow chart diagram depicting the overview of dialog creation and is referenced with more particularity in FIG. 4. Referring to FIG. 2, a patient 100 reports on a specific aspect of care 110 (i.e., foot care in a Diabetes Structure) that is addressed by a dialog 125, the smallest content structure of the system, from a disease specific library 120. The basic format of each dialog includes questions 130 related to patient self-management behaviors 132, patient-reportable symptoms 134, or patient knowledge 136. Each question provides a choice for an answer ("output variable") 140 that falls into one of three risk categories; high 142 medium 144 and low risk 146. For each risk category there is an associated follow up 150 which is a teaching statement 152, a motivational statement 154 or a new question 156 that explores the patient's condition in more depth.

While the logical branching within a dialog depends on output variables, no dependency exists between individual dialogs. Dependencies for dialogs exist outside the dialog structure in related operators.

Figure 3:
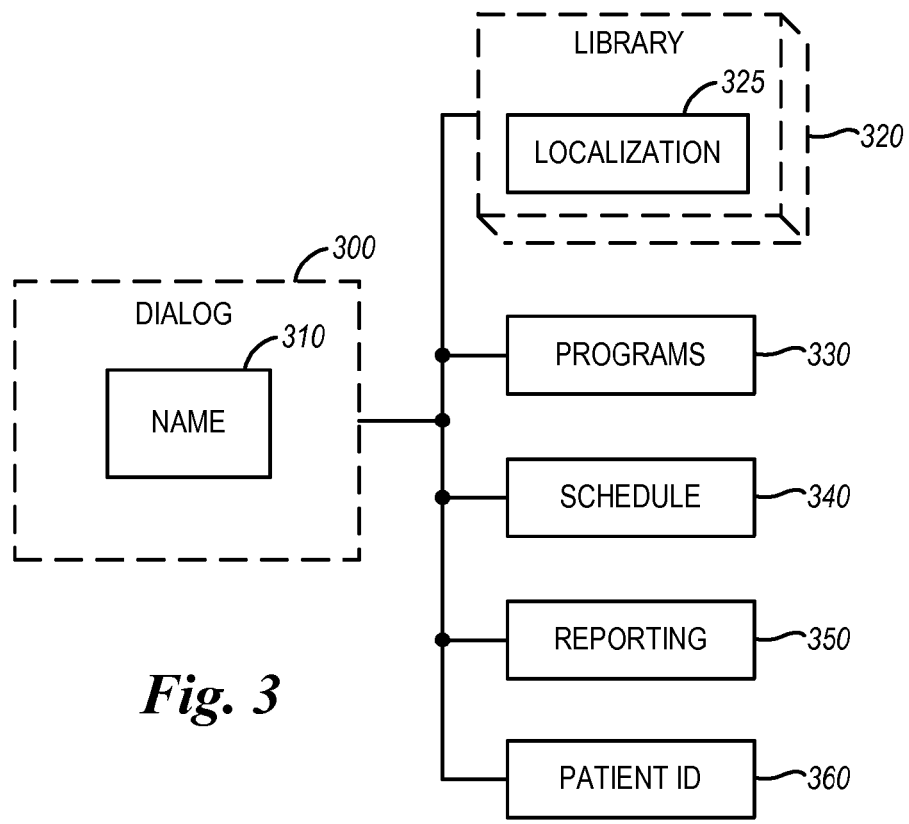
FIG. 3 is a block diagram depicting an interdependent characteristics (operators) of a dialog.

FIG. 3 is a block diagram depicting the interdependent characteristics (operators) of a dialog 300 in the system matrix. The interdependent characteristics include a Name Label 310 for the aspect of care addressed, a Library 320 that houses a body system specific Localization 325, client specific Programs 330 in which the dialog is being used (referenced), a Schedule frequency 340 by which the dialog is being displayed to a patient in a specific program, definition of Reporting requirements 350, and Patient Identification information 360 and metrics of each individual appliance to which the dialog is assigned.

The user interface is easy to use due to the simplicity of program structure in which the user is able to interface with the program and dialog composition aspects of the system. Simply using drag and drop content selection procedures based on a medical decision creates a process familiar to the user. The user decides what aspects of care are relevant for a given program or for an individual patient and in most cases simply selects existing content based on that decision. In all steps of dialog composition, certain steps are taken to make available the dialog in a content library.

FIG. 4 is a flow chart depicting the steps in creating and storing of content data from a dialog, a user's first task is to name the dialog-to-be-created as depicted in block 400. Next, the user defines the library section of block 410, in which the dialog will reside. The user then identifies an aspect of care at block 420 to which the dialog will primarily refer. Once the naming conventions are assigned and the aspect of care is chosen, the user creates dialog programming statements at block 430, in a graphical programming environment as embodied in FIG. 5. New dialog content is then stored in an appropriate user library at block 440.

Figure 5:
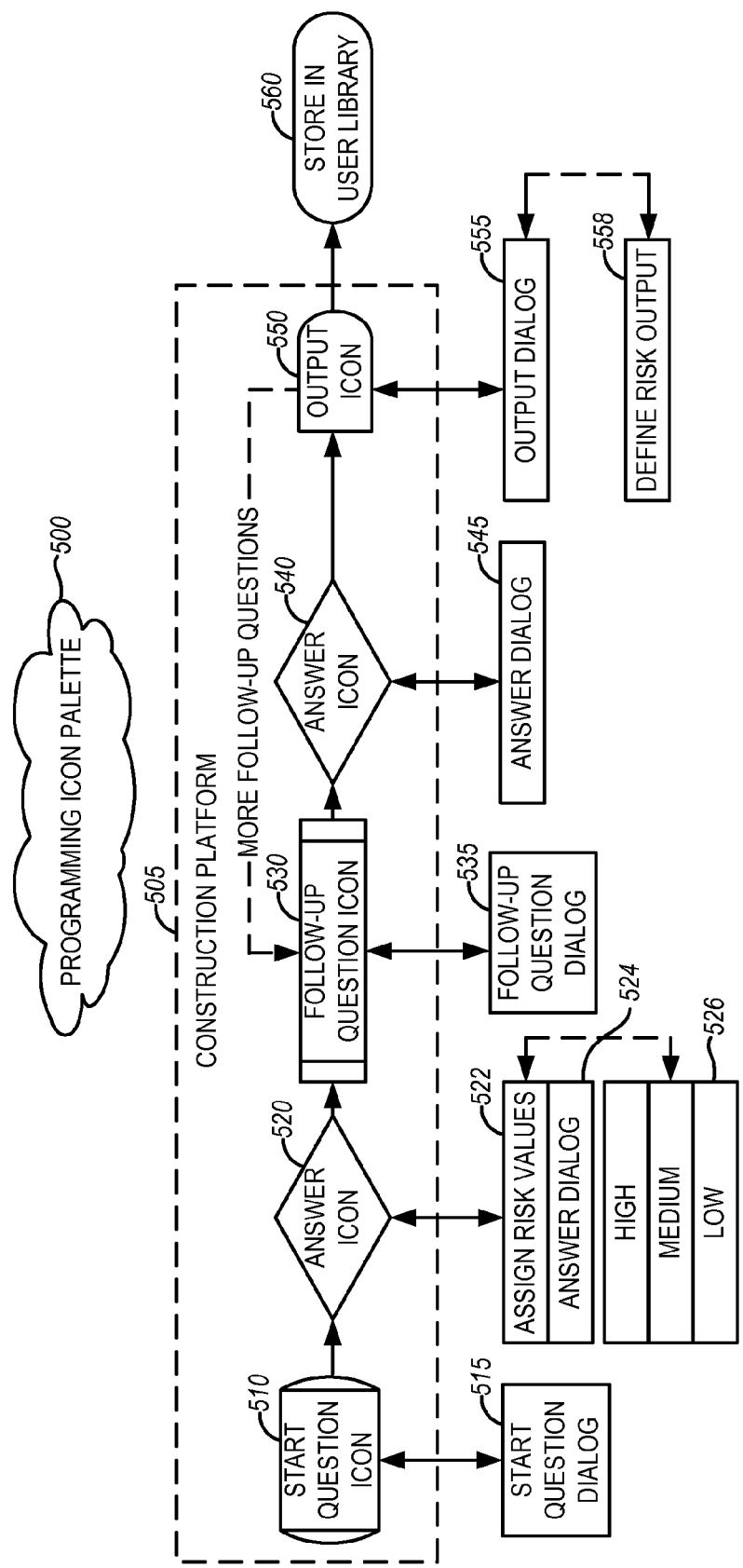
FIG. 5 is a flow chart diagram depicting the creation of the programming statements using a Dialog Editor Platform.

The user who has access to create new content does so using a simple dialog composer as embodied in FIG. 5. FIG. 5 is a diagram depicting the creation components of a dialog Editor Platform. First, a user is presented with a palette 500 of programming statements that are represented as graphic symbols (icons) that can be dragged from the palette of available statements into a dialog construction platform 505. In a typical embodiment of the present invention, the user drags a start question icon 510 and a three pronged answer icon 520 from an icon palette down to the construction platform 500. The user then activates a dialog box for each icon by clicking on it with a mouse and specifying a question associated with that particular icon, for example, a Start Question Dialog 515. Next, in an Answer Dialog 524, the user enters three answer options relative to the start question and assigns a raw risk value to each answer 526. The risk values are assigned from high to low with a corresponding text answer. "Yes" equals low risk and "no" equals high risk and "medium" equals somewhere in the middle of low and high risk. Follow up questions icons 530 are dragged onto the construction platform along with an associated answer icon 540. An answer dialog 545 is then prepared. Clicking on the output icon 550, the user activates the output dialog box 555. Here the user defines risk state output 558 in detail, further depicted with more particularity in FIG. 5, defining the position of the answer relative to the axis of the risk cube. At any time during or after the dialog creation process, the user can review the dialog created, using a simulation interface to an appropriate appliance or in the alternative, the user can review the actual dialog content in a text only overview window. Once all the follow up questions, answers and output dialogs are formulated and put onto the construction platform 525, the newly created dialogs are store in a user library 560 from where it can be referenced for participation in any user defined care management program or for later updating or editing.

Figure 6:
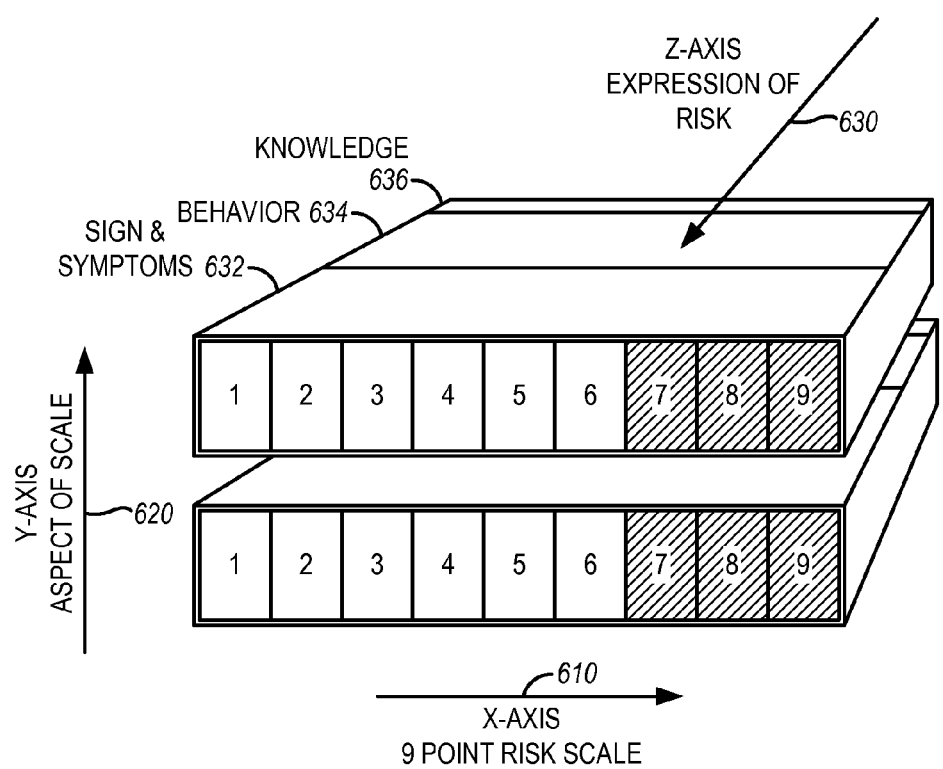
FIG. 6 is a block diagram illustrating the three dimensional aspects of the dynamically determined risk state output scale.

FIG. 6 is a block diagram illustrating the three dimensional aspects of the dynamically determined risk state output scale which in the Dialog Composer, FIG. 5, is referenced at block 558. The X-axis 610 scales whether the answer to a question dialog sets the risk at a certain risk level on a 9 point risk scale or whether the answer moves the patient risk state in a certain direction and by how much, thereby creating an accumulated risk profile. Additionally, the answer to a dialog is incorporated as a value in a mathematically calculated risk state that may incorporate other answers as well, creating a composite, weighted risk state. The Y-axis 620 refers to the actual aspect of care in which the risk will be incorporated. The Z-axis 630 incorporates the expression of risk 530, i.e, whether the risk is assigned to a sign or symptom 632, a behavior 634, or a knowledge expression 636. This dynamic model allows for very sophisticated risk profiling including risk trend alerts, composite risk profiling by aspects of care and profiling by risk expression. The dynamic risk "foot prints" available at any time can serve as triggers for automated content selection.

Once dialogs are named, created and assigned to an aspect of care and the risk output is assigned to the appropriate dialog, a user of the system can then use the Program Composer 30 to create the program that eventually is assigned to a patient.

FIG. 7 is a flowchart depicting the creation of "programs" using the Program Composer User Interface ("UI"). The UI is a platform for selecting library resident Dialogs created as depicted in FIG. 6, for participation in user-defined care management programs. In a typical embodiment of the present invention, the first step is to name the future program block 700. Next, at block 710, a user selects the disease libraries from which the program dialogs are created. Simultaneously, at block 720, the user checks the Utilities Library to add dialogs to the program that are not disease specific like generic greetings. This gives the user access to the detailed content of both of these libraries organized by aspects of care and their respective dialogs. Creating the program is now a simple task of adding dialogs to the program list, see block 730, and at block 740 to define the delivery of the dialogs as a user can choose specific delivery of the dialogs on a daily 750, weekly 752, or any other 754 programmed timed basis. Additionally, at block 742, a user checks the priority of dialogs to set parameters necessary for the correct scheduling of the dialogs in the program. Options are to force the scheduler to include the dialog block 744, or to assign dialogs as fillers, block 746. The later could be the case, for example, with trivia type dialogs, entertainment dialogs etc. Also, the user has the opportunity to decide the placement of dialogs in daily sessions. Greetings, for example, should be checked as "always first." The user can review the complete created program using the "View Selection" link, block 760. Using a very simple interface, the user has now created a totally custom made program. At block 770, the program is now available for assignment to any of the user's patients or for later modification by the user by adding or deleting dialogs. The present invention embodies the assignment by way of a Linker User Interface ("Linker UI") as depicted in FIG. 8.

FIG. 8 is a flow chart depicting the Linker UI, which is a platform for assigning or "linking" care management programs to patient populations or to individual patients. The first step at block 800 is to retrieve patient's name(s) to be used on the work platform through a filtering or sorting procedure defined by the user. Next, at block 810, the user marks the patient(s) and the care management program to be assigned. Finally the user creates the "Link" to activate a dialog box that allows the user to specify a time frame in which the program will run for the selected patient(s), block 820. Should the user wish to link the patient to other programs all that is needed is to repeat the process. To process the linking of an entire population or part of a population a user selects all patients, block 800, and assigns all of them, block 810, to a program.

The last step in the creation of a system program is the creation of a Reporter User Interface ("Reporter UI") which creates patient reports specific to patient results that in turn can initiate program actions based on those results. FIG. 9 is a flow chart depicting the Reporter UI and the creation of reports. The layout of the Reporter UI is completely consistent with that of the Linker UI depicted in FIG. 8. First a user retrieves patient names through a filtering process, block 902. The user filters, at block 900, names through the programs by either risk search, block 904, the aspects of care, block 905, within each program, or the risk expression, block 906, as defined as a symptom, behavior or knowledge, block 908, factor. This is done to allow a user to trend a risk profile, block 910, for the patient in the aspect of care where the patient has scored, for example, a high-risk profile as depicted in FIG. 6. A user can configure the Reporter UI to display block 920 the actual answers or results that led to the exampled high-risk profile. Lastly, at block 930, a patient is assigned to a program based on the risk profile or Aspect of Care. Reports assigned to patients can now for example, allow the user to see details for each aspect of care, order a report printed or write a note that will be associated with a linked event.

While this invention has been described in terms of several preferred embodiments, there are alterations, permutations, and equivalents that fall within the scope of this invention. It is therefore intended that the following appended claims be interpreted as including all such alterations, permutations, and equivalents as fall within the true spirit and scope of the present invention.

What is claimed is:

1. A server comprising:
    a questionnaire generator for (i) generating a questionnaire comprising (a) one or more questions for determining an expression of risk for an individual, (b) a first number of answer options to each of said questions and (c) one or more follow-up actions, wherein said expression of risk concerns at least one of a physical condition of said individual, a mental condition of said individual, and a behavior of said individual, (ii) associating each of said answer options with one of a second number of values representing a level of risk, said second number of values being greater than said first number of answer options and (iii) transmitting said questionnaire from said server to an apparatus, wherein said apparatus is (a) associated with said individual and (b) remotely located from said server;
    a database in a storage medium, said database containing model information relating to (i) an aspect of care, (ii) said expression of risk and (iii) said level of risk; and
    a profile generator for (i) generating a profile for said individual based on said aspect of care, responses to said questions, said expression of risk and said level of risk associated with said individual and (ii) sending health related information to said individual based on said profile, wherein data relating to said physical condition of said individual comprises patient information from one or more medical claims received by said server from a medical claims paying organization associated with said individual.

2. The server of claim 1, wherein said profile of said individual is updated based on one or more follow-up responses.

3. The server of claim 1, wherein (i) said profile further comprises a language of said individual, and a current health condition of said individual and (ii) said questionnaire generator also tailors said questionnaire in dependence upon said language and said current health condition of said individual.

4. The server of claim 1, wherein said questionnaire generator further generates a motivational profile and a comprehension capacity profile of said individual based on said responses to said questions received by said server from said apparatus.

5. The server of claim 1, wherein said health related information comprises:
    a request for additional responses; and
    educational information.

6. The server of claim 5, wherein said educational information is received by said server from an external source.

7. The server of claim 1, wherein said data relating to said physical condition of said individual further comprises one or more measurements received by said server from a monitoring device connected to said apparatus.

8. The server of claim 1, wherein said data related to said physical condition of said individual further comprises medical information from electronic medical records received by said server from a services organization associated with said individual.

9. A method for providing customized health information to an individual, said method comprising the steps of:
    (A) generating a questionnaire comprising (i) one or more questions for determining an expression of risk for said individual, (ii) a first number of answer options to each of said questions and (iii) one or more follow-up actions, wherein said expression of risk concerns at least one of a physical condition of said individual, a mental condition of said individual, and a behavior of said individual;

(B) associating each of said answer options with one of a second number of values representing a level of risk, wherein said second number is greater than said first number;

(C) transferring said questionnaire from a server to an apparatus, wherein said apparatus is (i) associated with said individual and (ii) remotely located from said server;

(D) accessing a database in a storage medium, said database containing model information relating to (i) an aspect of care, (ii) said expression of risk and (iii) said level of risk;

(E) generating a profile for said individual based on said aspect of care, responses to said questions, said expression of risk and said levels of risk associated with said individual; and (F) sending health related information to said individual based on said profile, wherein data relating to said physical condition of said individual comprises patient information from one or more medical claims received by said server from a medical claims paying organization associated with said individual.

10. The method of claim 9, further comprising the step of: updating said profile after said server receives one or more follow-up responses.

11. The method of claim 9, further comprising the steps of: registering a language of said individual, and a current health condition of said individual in said profile; and tailoring said questionnaire to said individual in dependence upon said language and said current health condition of said individual.

12. The method of claim 9, wherein said health related information comprises:
a request for additional responses; and
educational information.

13. The method of claim 12, wherein said educational information is received by said server from an external source.

14. The method of claim 9, further comprising the step of: generating a report comprising said profile.

15. The method of claim 9, wherein said data relating to said physical condition further comprises one or more measurements received by said server from a monitoring device connected to said apparatus.

16. The method of claim 9, wherein said data relating to said physical condition of said individual further comprises medical information from electronic medical records received by said server from a services organization associated with said individual.

17. A storage medium for use in a server to communicate with one or more patient devices, the storage medium recording a computer program that is readable and executable by the server, the computer program comprising the steps of:

(A) displaying a plurality of icons of a plurality of questions, a plurality of answers, a plurality of follow-up actions and a plurality of follow-up answers;

(B) receiving a selection to each of a particular question of said questions, a particular answer of said answers, a particular follow-up action of said follow-up actions and a particular follow-up answer of said follow-up answers from a user;

(C) linking said icons of said particular question, said particular answer, said particular follow-up action and particular follow-up responses;

(D) converting said linked icons into a questionnaire; and (E) transmitting said questionnaire to said one or more patient devices over a communication network.

18. The storage medium of claim 17, wherein the computer program further comprises the step of:
assigning a position of said particular answer along a risk scale ranging from a low risk value to a high risk value.

19. The storage medium of claim 17, further comprising the steps of:
registering a language of an individual and a current health condition of said individual in a profile; and
tailoring said computer program to said individual in dependence upon said language and said current health condition of said individual.

20. The storage medium of claim 17, further comprising the step of:
simulating said questionnaire prior to said transmission of said questionnaire to said one or more patient devices.

* * * * *